10/29/85 XR 4,549,533

United States Patent [19]

Cain et al.

[11] Patent Number: 4,549,533

[45] Date of Patent: Oct. 29, 1985

[54] APPARATUS AND METHOD FOR GENERATING AND DIRECTING ULTRASOUND

[75] Inventors: Charles A. Cain, Urbana; Leon A. Frizzell, Champaign, both of Ill.

[73] Assignee: University of Illinois, Urbana, Ill.

[21] Appl. No.: 574,930

[22] Filed: Jan. 30, 1984

[51] Int. Cl.[4] .......................... A61B 5/00; A61H 1/00

[52] U.S. Cl. .................................. 128/24 A; 128/660; 310/320; 73/626

[58] Field of Search ............. 128/660, 24 A; 310/320, 310/367, 334–337; 73/620, 625–626, 642, 644

[56] References Cited

U.S. PATENT DOCUMENTS

| | | | |
|---|---|---|---|
| 3,569,750 | 3/1971 | Beaver | 310/320 |
| 3,833,825 | 9/1974 | Haan | 310/320 |
| 4,240,295 | 12/1980 | Uranishi | 128/660 |
| 4,254,661 | 3/1981 | Kossoff et al. | 73/625 |
| 4,350,917 | 9/1982 | Lizzi et al. | 128/660 X |
| 4,441,486 | 4/1984 | Pounds | 128/24 A |
| 4,478,085 | 10/1984 | Sasaki | 73/642 |

OTHER PUBLICATIONS

Lehmann, J. F., "Therapeutic Heat and Cold", Williams & Wilkins Publ., Baltimore, TM 1982, pp. 522–530.

Beard, R. E. et al, "An Annular Focus UTS Lens for Local Hyperthermia", UTS in Med. & Biol., vol. 8, #2, pp. 177–184, 1982.

*Primary Examiner*—Kyle L. Howell
*Assistant Examiner*—Francis J. Jaworski
*Attorney, Agent, or Firm*—Martin M. Novack

[57] ABSTRACT

The disclosed apparatus of the invention operates to generate and direct ultrasound over predetermined regions of a body, such as a programmed sequence of target points. A plurality of side-by-side tapered piezoelectric transducer elements are provided. Means are provided for energizing the transducer elements with electrical energy having a variable frequency. The frequency of the electrical energy is varied to change the direction of the ultrasound produced by the transducer elements. In the preferred embodiment of the invention, a processor is responsive to a coordinate of an input target point for controlling the variation of frequency. In one form of the invention, means are provided for varying the relative phases of the electrical energy applied to the transducer elements. In this form of the invention, the processor means is also responsive to at least another coordinate of the input target point for controlling the variation of the relative phases. In another form of the invention, means are provided for selectively enabling at least one of the transducer elements. In this embodiment, each of the transducer elements has an associated focusing lens, and the processor is responsive to a coordinate of the input target point for controlling the selective enablement.

31 Claims, 8 Drawing Figures

APPARATUS AND METHOD FOR GENERATING AND DIRECTING ULTRASOUND

BACKGROUND OF THE INVENTION

This invention relates to apparatus for generating and directing ultrasound energy and, more particularly, to an apparatus which is addressable to direct an ultrasonic beam to a specified region of a body, such as for selectively heating the specified region of the body.

The use of ultrasonic energy for diagonostic and for treatment purposes has come into widespread use. In diagnostic systems, ultrasound energy is directed into a body, and the characteristics of the ultrasound energy either transmitted through the body or reflected from the body are used to obtain information about the body's structure. In some systems, images of the internal body structure are formed, whereas other systems are non-imaging.

In treatment systems, ultrasonic energy is utilized to selectively heat an internal region of the body. A highly focused and powerful beam may be used to "burn out" undesired tissue, such as a tumor. Alternatively, a defined region of the body may be brought to a controlled elevated temperature for a relatively long period of time to obtain a desired effect, such as the demise, retardation of growth, or other change in nature of undesired cells in the region. These techniques are known generally as regional hyperthermia.

In applicatins where ultrasonic energy is used to obtain a controlled heating pattern in a defined region of a body, it is generally desirable to form a beam of ultrasound energy that can be accurately directed to the body region to be heated, and accurately movable over the region to obtain a desired heating pattern. There are various known prior art techniques for generating focused ultrasound beams that can be directed to a specific position in a body or can be scanned over a desired pattern in the body. Most such systems suffer one or more of the following disadvantages: lack of accuracy, lack of operator flexibility in directing the beam, unreliability, and undue complexity or expense.

It is among the objects of the present invention to provide a system which overcomes these disadvantages.

SUMMARY OF THE INVENTION

The present invention involves an apparatus and method for generating and directing, under operator control, a beam of ultrasound energy. The invention can be used for various applications in which an ultrasound beam is generated and directed to operator-selected regions of a body, but the invention has particular application for hyperthermia, wherein a defined body region is to be heated to a controlled temperature.

The apparatus of the invention operates to generate and direct ultrasound over predetermined regions of a body, such as a programmed sequence of target points. A plurality of side-by-side tapered piezoelectric transducer elements are provided. Means are provided for energizing the transducer elements with electrical energy having a variable frequency. The frequency of the electrical energy is varied to change the direction of the ultrasound produced by the transducer elements.

In the preferred embodiment of the invention, a processor means is responsive to a coordinate of an input target point for controlling the variation of frequency. In one form of the invention, means are provided for varying the relative phases of the electrical energy applied to the transducer elements. In this form of the invention, the processor means is also responsive to at least another coordinate of the input target point for controlling the variation of the relative phases.

In another form of the invention, means are provided for selectively enabling at least one of the transducer elements. In this embodiment, each of the transducer elements has an associated focusing lens, and the processor is responsive to a coordinate of the input target point for controlling the selective enablement.

Further features and advantages of the invention will become more readily apparent from the following description when taken in conjunction with the accompanying drawings.

DESCRIPTION OF THE PREFERRED EMBODIMENTS

Figure 1:
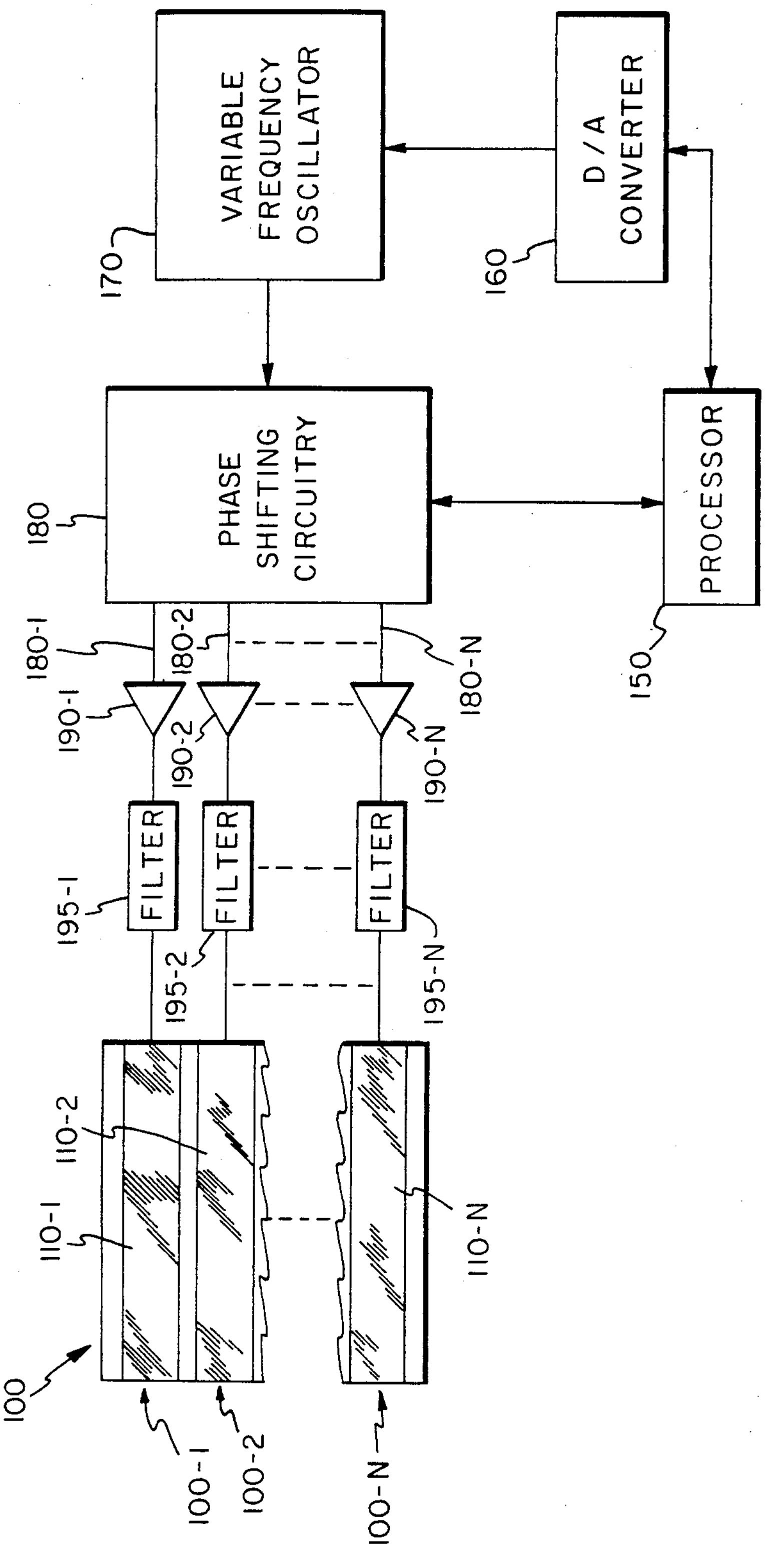
FIG. 1 is a block diagram, partially in schematic form, of an apparatus in accordance with an embodiment of the invention.
Figure 2:
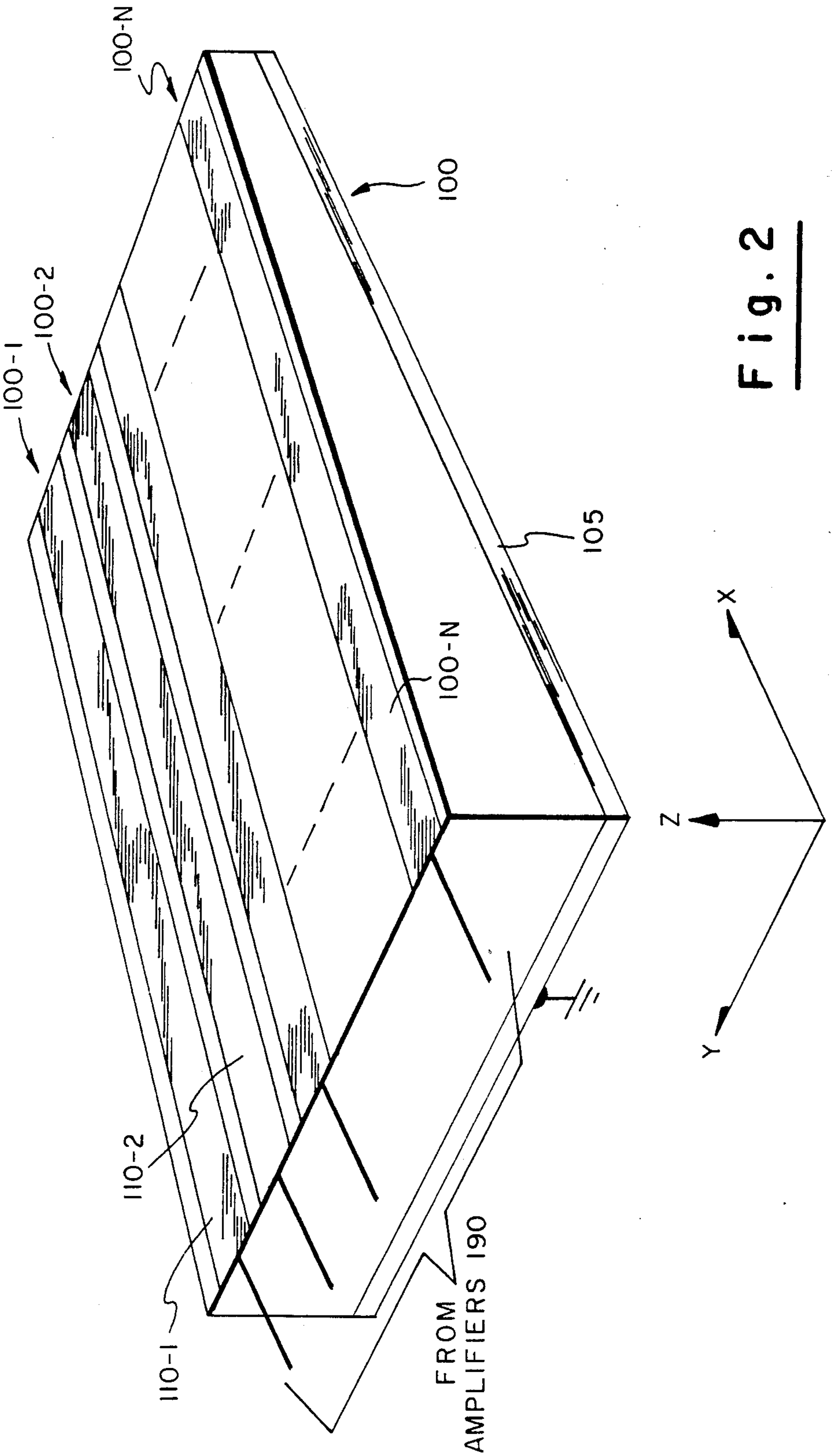
FIG. 2 is a perspective view of the transducer elements of the FIG. 1 embodiment.

Referring to FIG. 1 there is shown an embodiment of an apparatus in accordance with the invention which can be used, inter alia, for hyperthermia treatment of a selected body region in accordance with the method of the invention. A transducer 100 is provided, and is shown in further detail in FIG. 2. The transducer 100 comprises a tapered wedge of piezoelectric material such as lead zirconate titanate which is tapered along the x direction. A metal common electrode 105 is disposed on the bottom surface of the wedge, and parallel metal electrodes 110-1 through 110-n, are disposed on the opposing tapered surface of the wedge. The electrodes 110-1 through 110-n can be independently energized, so that the transducer structure of FIG. 2 effectively includes n side-by-side tapered piezoelectric transducer elements 100-1 through 100-n which can be individually excited. Alternatively, the transducer elements can be acoustically decoupled by cutting partially or totally through the thickness of the ceramic between the elements. If the ceramic is cut completely through, the elements can be mounted on a support material (e.g. applied to the top surface), with a ground foil on the bottom surface.

In the FIG. 1 embodiment a processor 150 is utilized to control the directing of the ultrasound beam toward an operator-selected target "point" within the body. (The elemental region to which the ultrasound can ultimately be focused will, of course, in any practical system, be of a finite size that depends on various system parameters.) The points at which the beam is directed can be individually selected or can be part of a programmed heating pattern, although the present invention does not, per se, deal with the particular manner in which the target point or pattern is selected. In the present embodiment the processor 150 is a general purpose digital processor, such as a model 8031/8051 manufactured by Intel Corp., but it will be understood that any suitable general or special purpose processor, digital or analog, can be utilized consistent with the principles of the invention. The digital processor 150 would conventionally include associated memory, timing and input/output devices for communicating therewith (not shown).

An output of the processor 150 is coupled, via a digital-to-analog converter 160, to a variable frequency oscillator 170. The output of oscillator 170 is coupled to phase shifting circuitry 180, which is also under control of the processor 150. The phase shifting circuitry 180 has outputs designated 180-1 through 180-n, which are respectively coupled via amplifiers 190-1 through 190-n and filters 195-1 through 195-n to electrodes 110-1 through 110-n of transducer elements 100-1 through 100-n.

In broad terms, operation of the system of FIG. 1 is as follows: The position from which a transducer of varying thickness radiates with maximum efficiency will be a function of the operating frequency, since there will be a resonance, for a given frequency, at a particular thickness. Accordingly, the x position in the treatment field is determined by the frequency of the variable frequency oscillator 180. The phase selection circuitry is used to control the phase of the energizing signals coupled to each transducer element in order to focus and direct the beam toward a particular y-coordinate and depth in the body (z-coordinate), in the manner of phased array steering. Accordingly, a specified beam target position is achieved under control of processor 150 which controls the frequency output of variable frequency oscillator 170 and also controls the phase selections of phase shifting circuitry 180.

Figure 3:
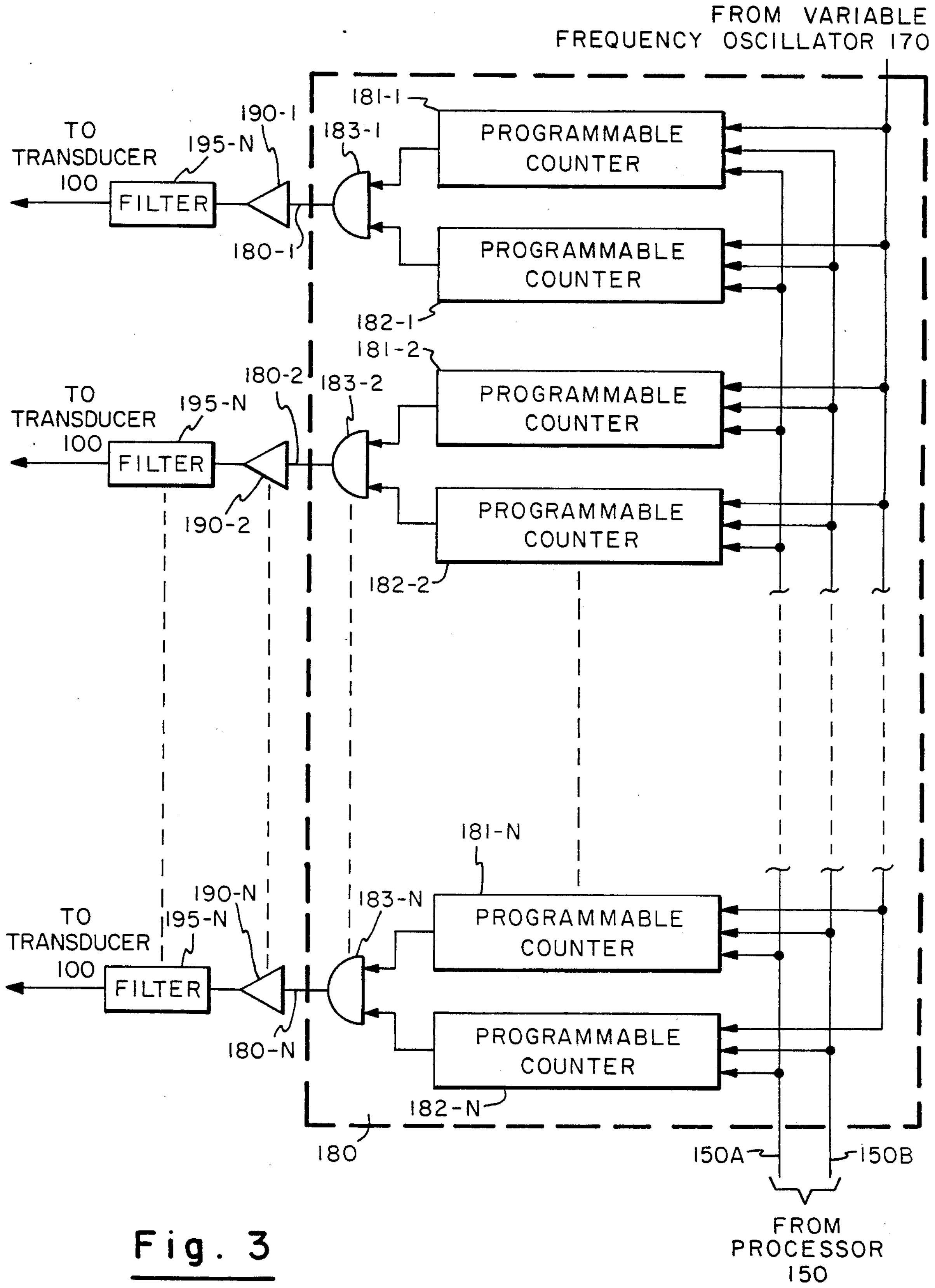
FIG. 3 is a block diagram of the phase shifting circuitry of the FIG. 1 embodiment.

The invention is not directed, per se, to any particular type of phase shifting circuitry 180. An embodiment of a suitable type of phase shifting circuitry 180 is illustrated in FIG. 3. The output of the variable frequency oscillator 170 is coupled to pairs of programmable digital counters 181-1, 182-1 through 181-n, 182-n. These counters may be, for example, type 10136 Universal Hexidecimal Counters sold by Motorola Corp. Each of the programmable counters receives the output of the variable frequency oscillator 170. Each of the counters also receives, from processor 150, an input addressing signal, via input addressing lines 150*a*, and an initial state signal, via initial state lines 150*b*. The outputs of the pairs of counters 181-1, 182-1 through 181-n, 182-n are coupled to the inputs of respective AND gates 183-1 through 182-n. The outputs of the AND gates 183-1 through 183-n are respectively coupled to the amplifiers 190-1 through 190-n, and then filters 195-1 through 195-n (FIG. 1).

In operation of the FIG. 3 circuit, each pair of programmable counters 181, 182 receives the oscillator signal and divides, down to a much lower frequency, by its characteristic count, L. The initial state lines 150*b* operate to load respective initial states, which can be designated M and N, into the pair of counters. The input addressing signals direct the initial state signals to the appropriate counters. The outputs of the counters are rectangular waves which are ANDed by the respective AND gate 182 associated with the pair of counters (181 and 182). It will be understood that the output of the AND gate 183 is a rectangular pulse having both phase and duty cycle which depend upon the initial states loaded into the pair of counters. The relative phase and duty cycle can be expressed as follows:

$$\text{phase} = \frac{2\pi}{L}\left(\frac{M+N}{2}\right) \text{ radians}$$

$$\text{duty cycle} = \cos\left[\frac{2\pi}{L}\ \frac{(N-M)}{2}\right]$$

The outputs of AND gates 182 are coupled to amplifiers 190 and then filters 195, and the filters operate to pass the fundamental frequency at which the rectangular pulses occur, but reject the higher harmonic components. This results in the output of each of the filters 195 being a substantially sinusoidal signal having an amplitude which depends on the duty cycle of the received rectangular pulses, and a phase which depends on the phase of the received rectangular pulses. Accordingly, by selecting the initial counts M and N respectively loaded into each pair of counters 181-1, 182-1 through 181-n, 182-n, the processor 150 can control the y and z coordinates, as well as the amplitude (if desired) of the ultrasound beam.

The manner of selecting phase shifts to focus and/or steer an ultrasound beam is well developed in the art, and the configuration of circuitry 180 shown herein is exemplary.

Figure 4:
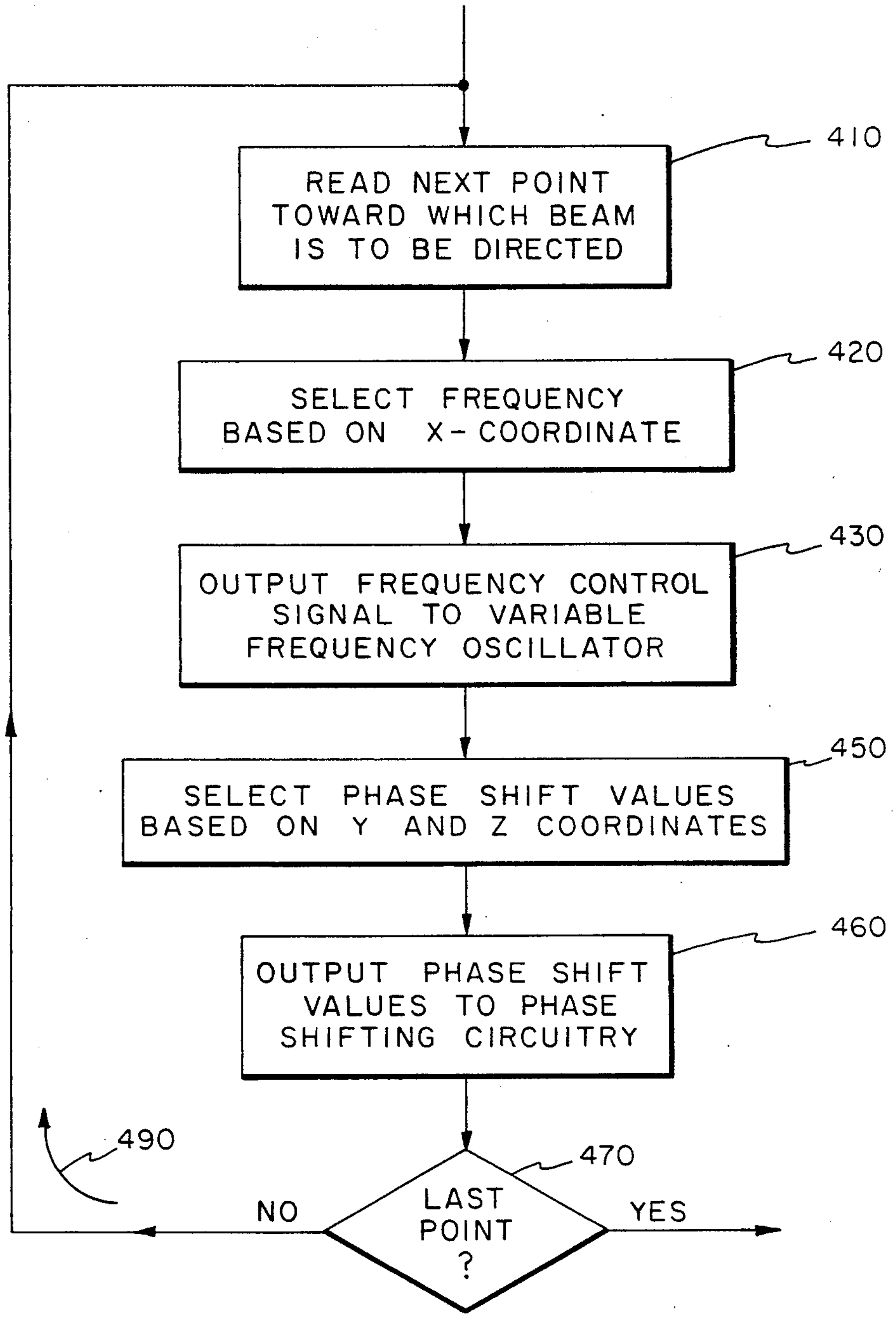
FIG. 4 is a flow diagram of a routine for the processor of the FIG. 1 embodiment.

Referring to FIG. 4, there is shown a flow diagram of a routine suitable for programming the processor 150 to control operation of the FIG. 1 embodiment. The block 410 represents the reading of the next point toward which the beam is to be directed. As previously noted, the point may be, for example part of a predetermined, computed, or operator-selected heating pattern in a hyperthermia system. A particular point may be addressed for any desired period of time and at any desired amplitude of energization, consistent with the principles hereof. The x-coordinate of the point is then used to select the operating frequency (block 420). The relationship between excitation along the x axis and the beam position can be determined empirically, or by calculation or computer simulation, and then used for establishing a look-up table as between x-coordinate and the required oscillator frequency. The frequency control signal is then output (block 430) to the variable frequency oscillator 170, via the digital-to-analog converter 160. The block 450 is then entered, this block representing the selection of phase shift values based on the y and z-coordinates of the input target point. The block 460 represents the outputting of the selected phase shift control signals to the phase shifting circuits 180. A determination is then made (diamond 470) as to whether or not there are further points to be addressed. If so, the block 410 is re-entered, and the loop 490 is continued for the target points to which the beam is to be directed.

Figure 5:
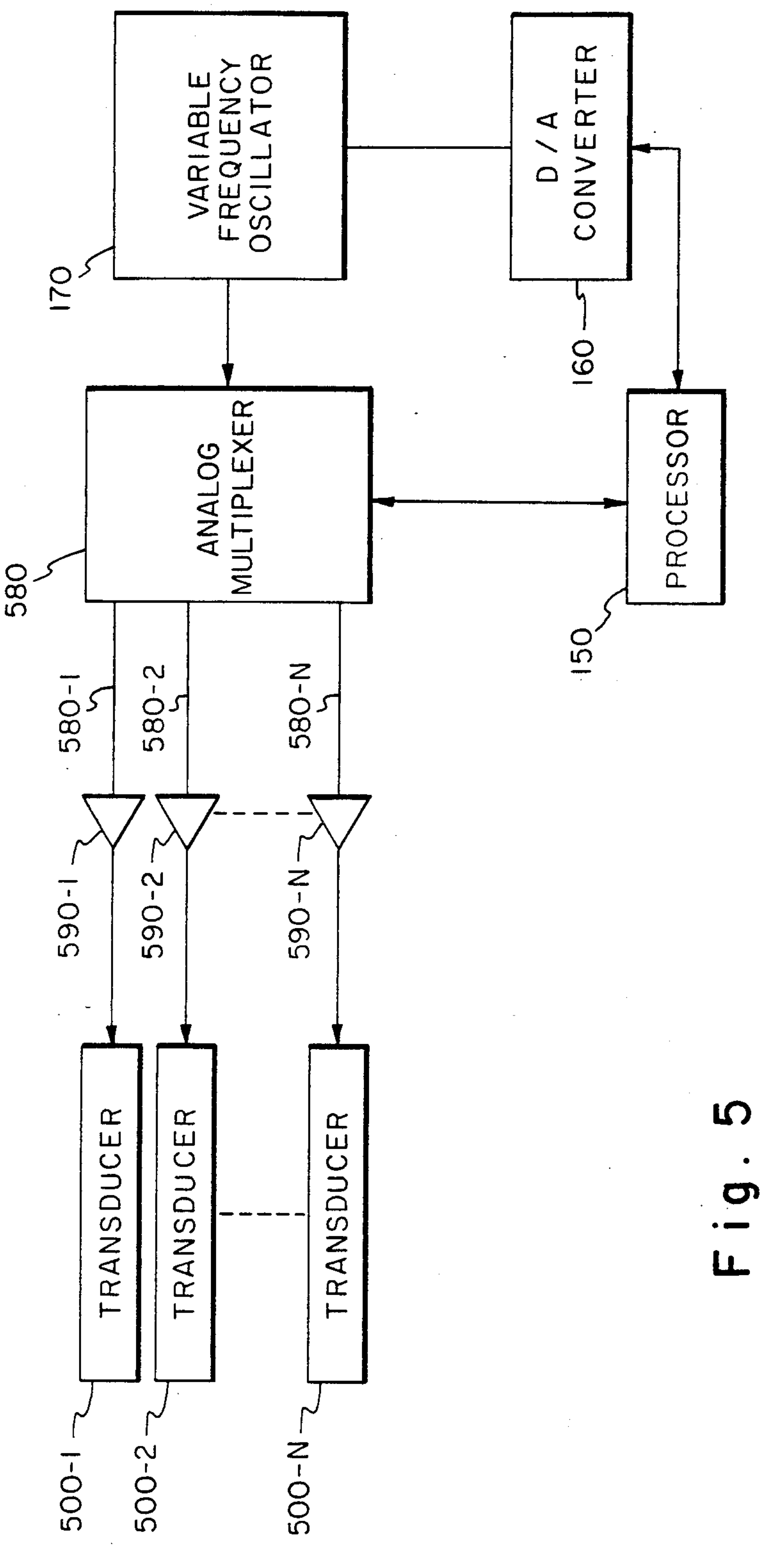
FIG. 5 is a block diagram of an apparatus in accordance with another embodiment of the invention.
Figure 6:
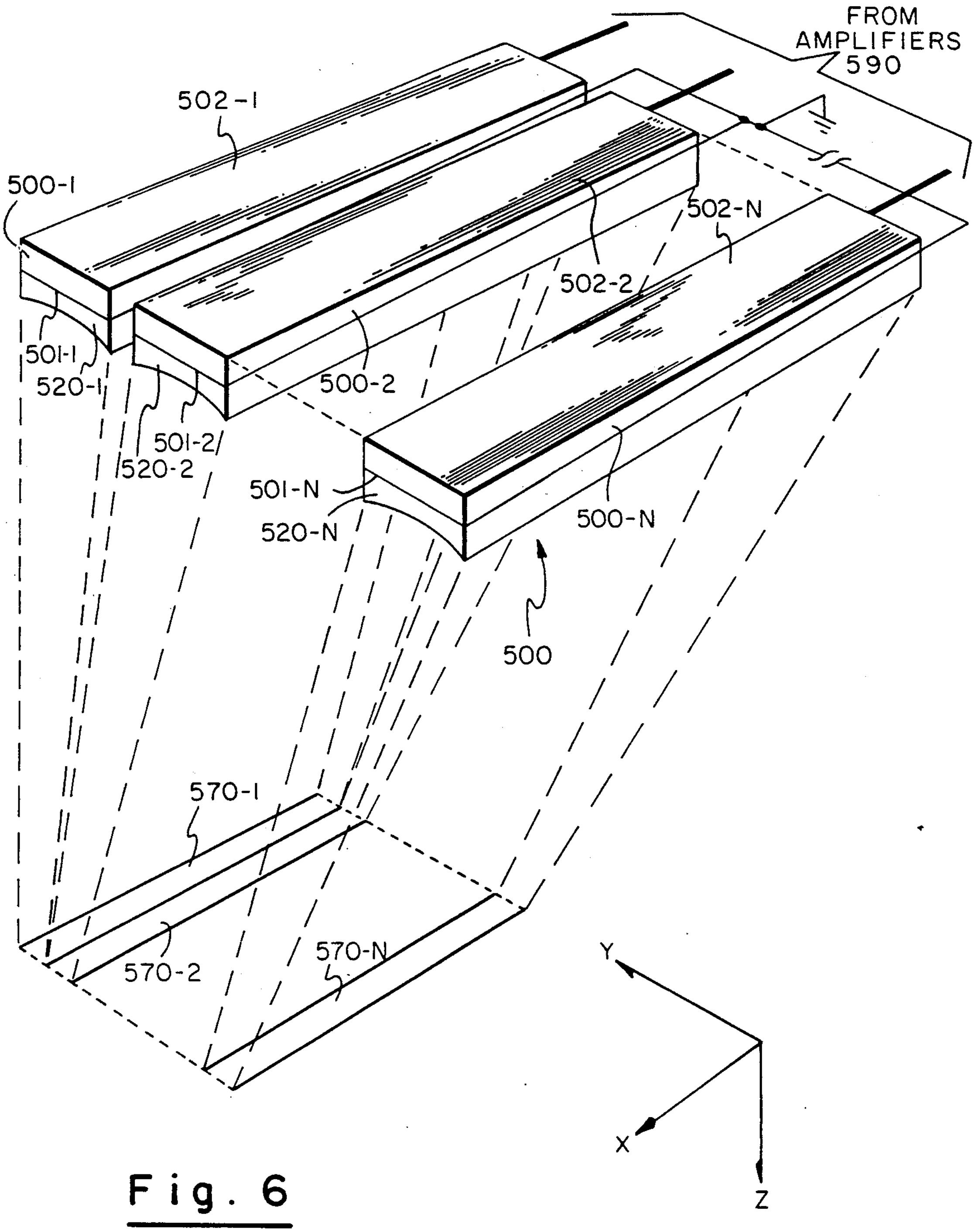
FIG. 6 is a perspective view of the transducer assembly of the FIG. 5 embodiment.

Referring to FIG. 5, there is shown an embodiment of an apparatus in accordance with another embodiment of the invention and which can be used to practice the method of the invention. In the embodiment of FIG. 5, a transducer assembly 500 includes tapered transducer elements 500-1 through 500-n which, as in the FIG. 1 embodiment, can be either transducer elements formed on a single wedge of piezoelectric material or, as shown in this case, separate piezoelectric elements. Each tapered transducer element (see FIG. 6) is provided with an electrically common electrode 501-1 through 501-n on one face thereof. (This electrode can be a single larger electrode if a single wedge of piezoelectric material is utilized.) The transducer elements have respective opposing electrodes 502-1 through 502-n on the tapered surfaces thereof, in the x-direction. In the FIG. 5 embodiment, the y-coordinate of a desired position is obtained by selection of a particular one (or more if desired, for a larger target region) of the transducer elements for excitation. Each transducer element strip 500-1 through 500-n has an associated cylindrical lens, 520-1 through 520-n which focuses the ultrasound energy from its associated transducer element to a focal strip, as represented in FIG. 6 by the strips 570-1 through 570-11. By selecting the operating frequency, as previously described, a target focal "point" or region can be preferentially selected. The depth in the body (z-coordinate) in this embodiment is a function of the lens parameters.

In the FIG. 5 embodiment, the processor 150 again controls the variable frequency oscillator 170 via the digital-to-analog converter 160. In this embodiment, however, the particular transducer element to be energized is determined by an n-channel analog multiplexer 580 which is under control of the processor 150 to select one or more of the outputs 580-1 through 580-n. The analog multiplexer 580 may be, for example, a type 4051, CMOS Series of RCA Corp. The n outputs of analog multiplexer 580 are respectively coupled to amplifiers 590-1 through 590-n which are, in turn, coupled to transducer elements 500-1 through 500-n.

Figure 7:
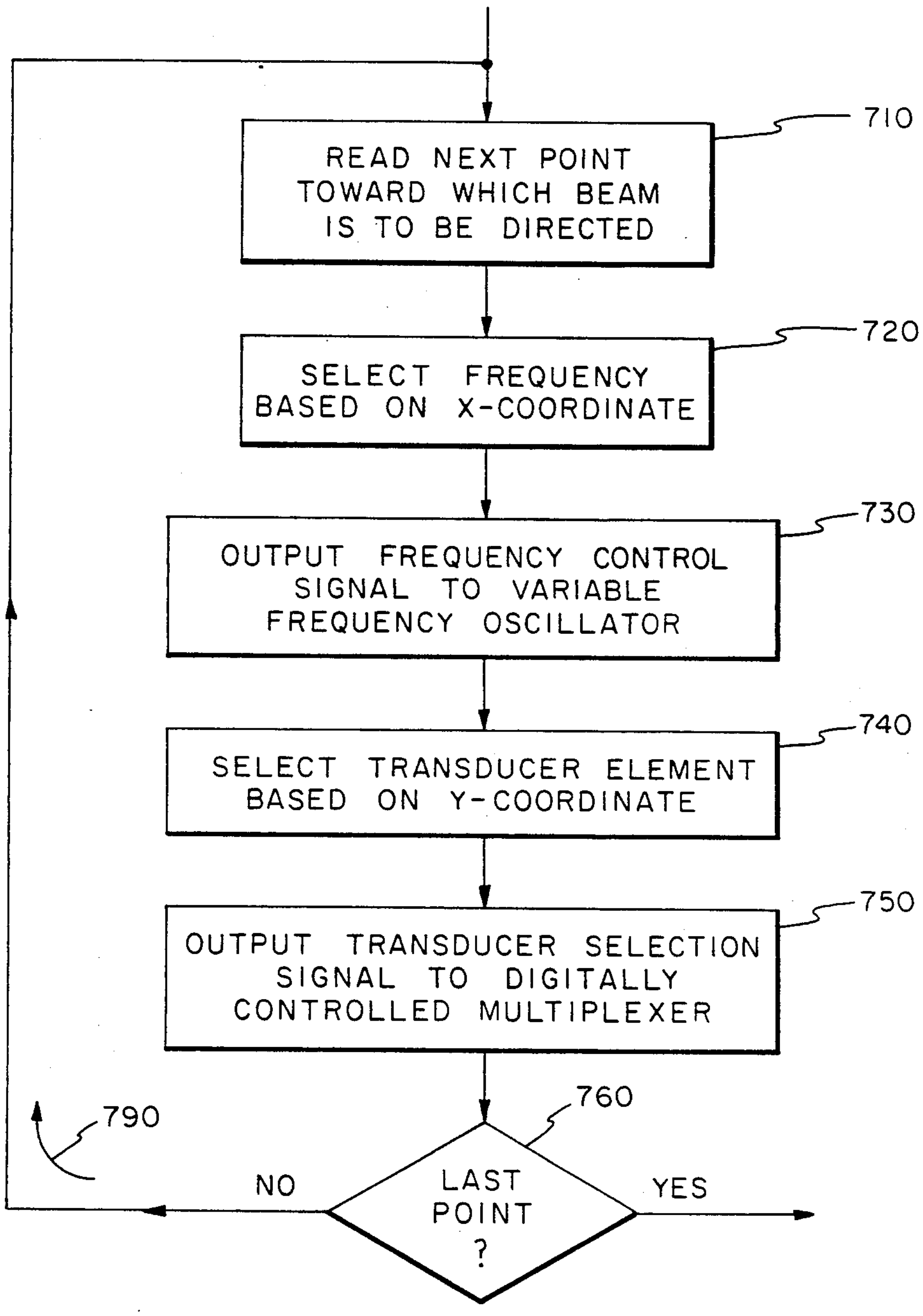
FIG. 7 is a flow diagram of a routine for the processor of the FIG. 5 embodiment.

Referring to FIG. 7, there is shown a flow diagram of a routine for controlling the processor in the FIG. 5 embodiment. The blocks 710, 720, and 730 are similar to the corresponding blocks 410, 420, and 430 of the FIG. 4 routine. In particular, in this portion of the routine, the next target "point" toward which the beam is to be directed is read in (block 710), a frequency is selected based on the x-coordinate (block 720), and the frequency control signal is output to the variable frequency oscillator 170 (block 730). The particular transducer element is then determined from the y-coordinate of the point at which the beam is to be directed. This is represented by the block 740. The control signal for the particular element is then coupled to analog multiplexer 580 (block 750), and inquiry is then made (diamond 760) as to whether or not there are further points to be addressed. If so, the block 710 is reentered, and the loop 790 is continued for the target points to which the beam is to be directed.

Figure 8:
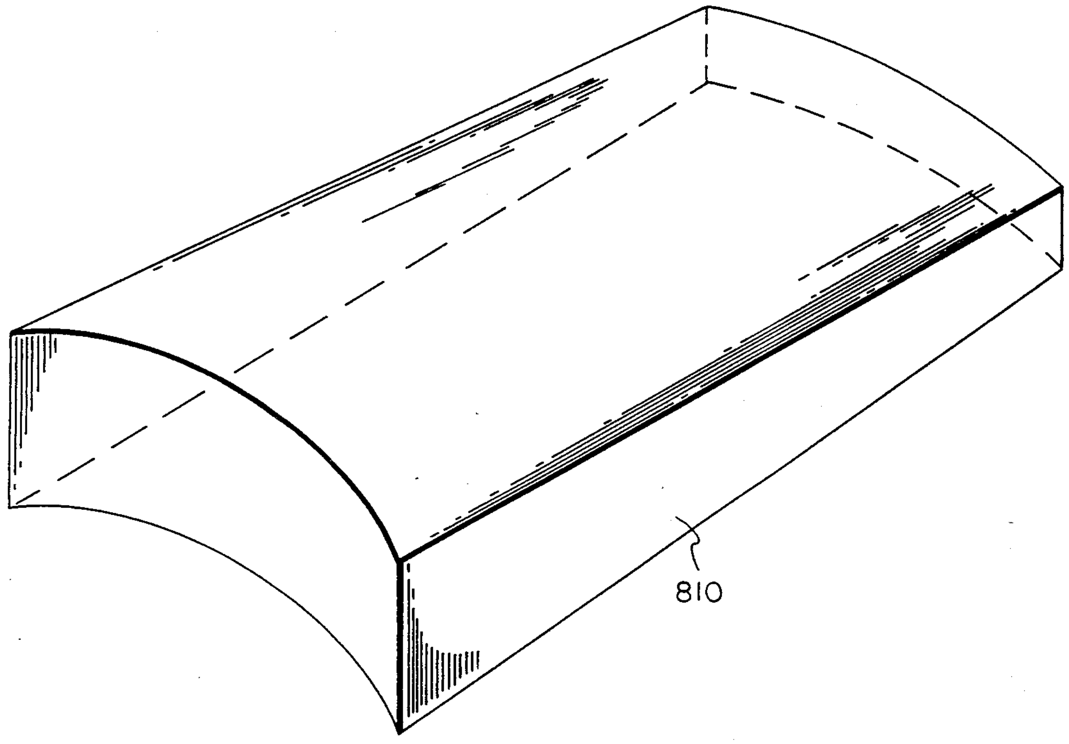
FIG. 8 shows a tapered curved transducer element.

The invention has been described with reference to particular preferred embodiments, but variations within the spirit and scope of the invention will occur to those skilled in the art. For example, the focusing means of the FIG. 6 transducer assembly could be alternatively provided without lenses by suitable curvature of the tapered transducer elements. FIG. 8 illustrates the shape of a curved wedge 810 on which electrodes can be applied. Also, it will be understood that multiple arrays can be employed, and that other combinations of electrical and lens focusing can be used, consistent with the principles hereof.

We claim:

1. Apparatus for generating and directing ultrasound at target positions, comprising:

a plurality of side-by-side piezoelectric transducer elements, each of said elements having tapered thicknesses;

variable frequency energizing means for energizing said transducer elements with electrical energy having a variable frequency;

means for controlling the frequency of said electrical energy so as to vary the target position of the ultrasound produced by said transducer elements along the direction of taper of said elements; and means for electronically varying the target position of the ultrasound produced by said transducer elements along a direction perpendicular to said direction of taper.

2. Apparatus as defined by claim 1, further comprising means for focusing the ultrasound produced by said transducer elements.

3. Apparatus as defined by claim 1, wherein said means for controlling the frequency of said electrical energy includes processor means responsive to a coordinate of an input target point for controlling the variation of frequency.

4. Apparatus as defined by claim 3, wherein said means for electronically varying the target position of the ultrasound along a direction perpendicular to the direction of taper includes means for varying the relative phases of the electrical energy applied to said transducer elements.

5. Apparatus as defined by claim 4, wherein said processor means is also responsive to at least another coordinate of the input target point for controlling the variation of said relative phases.

6. Apparatus as defined by claim 5, wherein said plurality of side-by-side tapered piezoelectric transducer elements comprise a wedge of piezoelectric material having spaced electrodes thereon.

7. Apparatus as defined by claim 6, wherein said electrodes comprise spaced parallel conductive strips disposed along the direction of taper.

8. Apparatus as defined by claim 7, further comprising a common electrode opposing said electrode strips.

9. Apparatus as defined by claim 3, wherein said means for electronically varying the target position of the ultrasound along a direction perpendicular to the direction of taper includes means for selectively enabling at least one of said transducer elements.

10. Apparatus as defined by claim 9, wherein said processor means is also responsive to another coordinate of the input target point for controlling said selective enablement.

11. Apparatus as defined by claim 10, wherein said piezoelectric transducer elements comprise separate wedge-shaped piezoelectric units, each unit having an associated focusing means.

12. Apparatus as defined by claim 1, wherein said means for electronically varying the target position of the ultrasound along a direction perpendicular to the direction of taper includes means for varying the relative phases of the electrical energy applied to said transducer elements.

13. Apparatus as defined by claim 1, wherein said plurality of side-by-side tapered piezoelectric transducer elements comprise a wedge of piezoelectric material having spaced electrodes thereon.

14. Apparatus as defined by claim 13, wherein said electrodes comprise spaced parallel conductive strips disposed along the direction of taper.

15. Apparatus as defined by claim 14, further comprising a common electrode opposing said electrode strips.

16. Apparatus as defined by claim 1, wherein said means for electronically varying the target position of the ultrasound along a direction perpendicular to the direction of taper includes means for selectively enabling at least one of said transducer elements.

17. Apparatus as defined by claim 16, wherein said piezoelectric transducer elements comprise separte wedge-shaped piezoelectric units, each unit having an associated focusing means.

18. Apparatus as defined by claim 1, wherein said piezoelectric transducer elements comprise separate wedge-shaped piezoelectric units, each unit having an associated focusing means.

19. Apparatus as defined by claim 18, wherein said focusing means comprises a focusing lens.

20. Apparatus as defined by claim 18, wherein said focusing means comprises a curvature of said wedge-shaped unit.

21. Apparatus for hyperthermia treatment of target points in a treatment region in a body, comprising:

a plurality of side-by-side piezoelectric transducer elements, each of said elements having tapered thicknesses;

a variable frequency source of electrical energy;

phase shifting means for receiving electrical energy from said variable frequency source and coupling said energy, at controllable relative phases, to said transducer elements; and processor means for deriving, from the coordinates of input target points, control signals for controlling the frequency of said variable frequency source and for controlling the relative phases of said phase shifting means whereby energy from said transducer elements is directed to a specified internal treatment region of the body for selective heating in the region.

22. Apparatus as defined by claim 21, wherein said plurality of side-by-side tapered piezoelectric transducer elements comprise a wedge of piezoelectric material having spaced electrodes thereon.

23. Apparatus for hyperthermia treatment of target points in a treatment region in a body, comprising:

a plurality of side-by-side piezoelectric transducer elements, each of said elements having tapered thicknesses;

a variable frequency source of electrical energy;

multiplexing means for receiving electrical energy from said variable frequency source and coupling said energy to a selected one of said transducer elements; and processor means for deriving, from the coordinates of input target points, control signals for controlling the frequency of said variable frequency source and for controlling the selection by said multiplexing means whereby energy from said transducer elements is directed to specified input target points in the internal treatment region for selective heating in the region.

24. Apparatus as defined by claim 23, wherein said piezoelectric transducer elements comprise separate wedge-shaped piezoelectric units, each unit having an associated focusing means.

25. Apparatus as defined by claim 24, wherein said focusing means comprises a focusing lens.

26. Apparatus as defined by claim 24, wherein said focusing means comprises a curvature of said wedge-shaped unit.

27. A method for hyperthermia treatment of target points in a treatment region of a body, comprising the steps of:

energizing a plurality of side-by-side piezoelectric transducer elements, each of said elements having tapered thicknesses, with electrical energy;

varying the frequency of said electrical energy to vary the target position of the ultrasound produced by said transducer elements along the direction of taper of said elements; and electronically varying the target position of the ultrasound produced by said transducer elements along a direction perpendicular to said direction of taper, whereby energy from said transducer elements is directed to a specified internal treatment region of the body for selective heating in the region.

28. The method as defined by claim 27, wherein said step of electronically varying the target position of the ultrasound produced by said transducer elements along a direction perpendicular to said direction of taper includes the step of varying the relative phases of the electrical energy applied to the transducer elements.

29. The method as defined by claim 28, further comprising the step of controlling said frequency and phase shifts in accordance with coordinates of target points in the treatment region.

30. The method as defined by claim 27, wherein said step of electronically varying the target position of the ultrasound produced by said transducer elements along a direction perpendicular to said direction of taper includes the step of selectively enabling one of the transducer elements.

31. The method as defined by claim 29, further comprising the step of controlling said frequency and selective enablement as a function of the coordinates of a target point in the treatment region.

* * * * *